(12) United States Patent
Quadri (10) Patent No.: US 7,425,219 B2
(45) Date of Patent: Sep. 16, 2008

(54) SYSTEM AND METHOD FOR ENDOLUMINAL GRAFTING OF BIFURCATED AND BRANCHED VESSELS

(76) Inventor: Arshad Quadri, 110 High Ridge Rd., West Hartford, CT (US) 06117

( * ) Notice: Subject to any disclaimer, the term of this patent is extended or adjusted under 35 U.S.C. 154(b) by 287 days.

(21) Appl. No.: 10/960,296

(22) Filed: Oct. 8, 2004

(65) Prior Publication Data
US 2005/0154444 A1 Jul. 14, 2005

Related U.S. Application Data

(60) Provisional application No. 60/509,904, filed on Oct. 10, 2003.

(51) Int. Cl.
*A61F 2/06* (2006.01)
(52) U.S. Cl. .................. 623/1.35; 623/1.13; 606/153
(58) Field of Classification Search ............ 623/1.13, 623/1.35–1.37; 606/153
See application file for complete search history.

(56) References Cited

U.S. PATENT DOCUMENTS

| 5,425,765 | A | 6/1995 | Tiefenbrun et al. |
| 5,464,449 | A | 11/1995 | Ryan et al. |
| 5,683,451 | A | 11/1997 | Lenker et al. |
| 5,797,952 | A | 8/1998 | Klein |
| 5,800,521 | A | 9/1998 | Orth |
| 5,824,041 | A | 10/1998 | Lenker et al. |
| 5,824,055 | A | 10/1998 | Spiridigliozzi et al. |
| 5,989,276 | A | 11/1999 | Houser et al. |
| 6,004,328 | A | 12/1999 | Solar |
| 6,039,749 | A | 3/2000 | Marin et al. |
| 6,068,637 | A | 5/2000 | Popov et al. |

(Continued)

FOREIGN PATENT DOCUMENTS

WO    WO 03/024307    3/2003

(Continued)

OTHER PUBLICATIONS

Patent Abstracts of Japan Publ. No. 2002-022062, Jan. 23, 2002.

(Continued)

*Primary Examiner*—Suzette J Gherbi
(74) *Attorney, Agent, or Firm*—Jacobson Holman PLLC (57) ABSTRACT

A system and method for endoluminal grafting of a main anatomic conduit in its diseased state in which it dilates to pose a life threatening condition and its various conduits that emanate from the main anatomic conduit. The grafting system comprises an endoaortic graft having at least one opening therein and at least one branch graft that is passable through the opening of the endoaortic graft into the branch anatomic conduit(s) such that the junction between the branch graft and the endoaortic graft is substantially fluid tight. A system and method for delivery of the endoaortic graft and also a system and method for efficient alignment and deployment of the branch (e.g., side branch) graft such that the coupling of the branch graft with the endoaortic graft is efficient and exact and fluid-tight; and a system and method for coupling the branch to the endoaortic graft via a coupling mechanism employing a memory metal alloy; a system and method for the proper and exact alignment of the endoaortic graft and the branch using magnetic force of a suitable nature, and which does not use the magnetic force as the coupling mechanism.

1 Claim, 11 Drawing Sheets

U.S. PATENT DOCUMENTS

| | | | |
|---|---|---|---|
| 6,068,654 A | 5/2000 | Berg et al. | |
| 6,074,416 A | 6/2000 | Berg et al. | |
| 6,090,128 A | 7/2000 | Douglas | |
| 6,123,723 A | 9/2000 | Kónya et al. | |
| 6,210,429 B1 | 4/2001 | Vardi et al. | |
| 6,217,585 B1 | 4/2001 | Houser et al. | |
| 6,280,467 B1 | 8/2001 | Leonhardt | |
| 6,293,955 B1 | 9/2001 | Houser et al. | |
| 6,302,906 B1 | 10/2001 | Goicoechea et al. | |
| 6,346,118 B1 | 2/2002 | Baker et al. | |
| 6,352,543 B1 * | 3/2002 | Cole | 606/153 |
| 6,428,565 B1 | 8/2002 | Wisselink | |
| 6,440,161 B1 | 8/2002 | Madrid | |
| 6,447,501 B1 | 9/2002 | Solar et al. | |
| 6,475,166 B1 | 11/2002 | Escano | |
| 6,508,835 B1 | 1/2003 | Shaolian et al. | |
| 6,514,281 B1 | 2/2003 | Blaeser et al. | |
| 6,517,574 B1 | 2/2003 | Chuter | |
| 6,572,645 B2 | 6/2003 | Leonhardt | |
| 6,579,305 B1 | 6/2003 | Lashinski | |
| 6,599,302 B2 | 7/2003 | Houser et al. | |
| 6,602,280 B2 | 8/2003 | Chobotov | |
| 6,652,567 B1 | 11/2003 | Deaton | |
| 6,660,030 B2 | 12/2003 | Shaolian et al. | |
| 6,663,665 B2 | 12/2003 | Shaolian et al. | |
| 6,666,884 B1 | 12/2003 | Webster | |
| 6,705,585 B1 * | 3/2004 | Roy | 251/11 |
| 6,767,359 B2 | 7/2004 | Weadock | |
| 6,908,477 B2 * | 6/2005 | McGuckin et al. | 623/1.11 |
| 7,131,991 B2 * | 11/2006 | Zarins et al. | 623/1.13 |
| 7,232,449 B2 * | 6/2007 | Sharkawy et al. | 606/153 |
| 7,241,300 B2 * | 7/2007 | Sharkawy et al. | 606/153 |
| 2001/0041902 A1 | 11/2001 | Lepulu et al. | |
| 2002/0072790 A1 | 6/2002 | McGuckin, Jr. et al. | |
| 2002/0143347 A1 | 10/2002 | Cole et al. | |
| 2002/0143383 A1 | 10/2002 | Parodi | |
| 2002/0156516 A1 | 10/2002 | Vardi et al. | |
| 2005/0149166 A1 * | 7/2005 | Schaeffer et al. | 623/1.13 |
| 2006/0282106 A1 * | 12/2006 | Cole et al. | 606/153 |
| 2007/0021753 A1 * | 1/2007 | Bolduc et al. | 606/104 |
| 2007/0167955 A1 * | 7/2007 | Arnault De La Menardiere et al. | 606/108 |

OTHER PUBLICATIONS

AneuRx Stent Graft—Product Features and Specifications and Surgical Techniques, www.medtronic.com/aneurx.

* cited by examiner

SYSTEM AND METHOD FOR ENDOLUMINAL GRAFTING OF BIFURCATED AND BRANCHED VESSELS

CROSS-REFERENCE TO RELATED APPLICATIONS

The present patent application is based on, and claims priority from, U.S. provisional Application No. 60/509,904, filed Oct. 10, 2003, which is incorporated herein by reference in its entirety.

BACKGROUND OF THE INVENTION

1. Field of the Invention

The present invention relates generally to medical devices and methods, and more particularly to a system and method for endoluminal grafting of blood vessels or other tubular, main anatomic conduits which have furcations or side branches extending there from.

2. Related Art

Endoluminal grafting is a relatively noninvasive method for placing a tubular graft within the lumen of a native, main anatomic conduit, such as a blood vessel. In certain cardiovascular applications of conventional or prior art techniques for endoluminal grafting, an endovascular graft may be implanted in the aneurismal segment of a blood vessel to form a prosthetic blood flow conduit through the aneurysm, and to effectively isolate the weakened portion of the blood vessel wall from hemodynamic forces and pressures of the flowing blood.

The prior art has included numerous endovascular grafts of varying design. In general, these endovascular grafts typically comprise a tube made of a pliable material such as PTFE, polyester, woven Dacron®, etc., in combination with a graft anchoring component (e.g., a stent, a frame, hooks, a series of wire rings, clips, staple, etc.) that operates to hold the grafts in its intended position within the blood vessel.

An example of a commonly used endovascular primary stent graft is the AneuRx stent graft sold by Medtronic. A sleeve may be used at the end of the graft if the graft itself is not sufficiently long. With or without the sleeve, a conventional endovascular stent graft requires the neck (the area of the vessel between the branches and the aneurysm) to be of sufficient size to permit attachment of the graft. A conventional endovascular stent graft cannot be used if the neck is too short (this problem is described in some detail in U.S. Pat. No. 6,428,565 to Wisselink, in the paragraph bridging columns 2 and 3).

Endovascular grafting is a clinically-acceptable alternative to traditional surgery in patients who suffer from aneurysms of the aorta. Indeed, many patients who are diagnosed with aortic aneurysms are relatively high-risk patients and may be classed as poor-risk for traditional surgery. If allowed to remain untreated, the aneurysm will surely dissect or rupture, causing a catastrophic event leading to significant risk of death to the patient. The traditional surgery in itself incurs significant risk of morbidity and mortality to the patient, due to its inherently extensive nature, which includes excessive blood loss, intra-operative heart attacks, and organ system ischaemias due to the cross-clamping of the aorta, which is an inherent part of the procedure. Thus, endovascular grafting offers a potential means of repair of aortic aneurysm without the risks and potential complication of traditional surgery. At the present time, endoluminal grafting can be performed in patients with aneurysms isolated to the infra-renal position or at the juxta-renal position with great benefit to the high-risk patients, but is not extendable to a large population of patients that suffer with aneurismal disease of the aorta that involves its major branches.

Depending on which region of the aorta is/are involved, the aneurysm may extend into areas of bifurcation (i.e., the inferior end of the aorta where it bifurcates into the iliac arteries) or segments of the aorta from which smaller branches extend. In this regard, aortic aneurysms can be classified into three basic types and five sub-types on the basis of the regions of the aneurismal involvement, as follows:

A. Thoracic Aortic Aneurysms:
 1. Aneurysms involving the ascending aorta
 2. Aneurysms involving the aortic arch and branches that emanate therefrom (i.e., subclavian artery, common carotid artery, innominate artery)
B. Thoracoabdominal Aortic Aneurysms: Aneurysms involving the descending thoracic aorta and arteries that emanate from it (i.e., thoracic intercostals arteries) and/or the supra-renal abdominal aorta and branch arteries that emanate therefrom (i.e., renal, superior mesenteric, celiac, and/or the intercostals arteries).
C. Abdominal Aortic Aneurysm:
 1. Aneurysms involving the para-renal aorta and the branches that emanate therefrom (i.e., the renal arteries).
 2. Aneurysms involving the infrarenal aorta with or without iliac involvement.

Unfortunately, not all the patients diagnosed with aortic aneurysm are presently considered to be candidates for endovascular grafting. This is largely due to the fact that most of the endovascular grafting systems are not designed for use in regions of the aorta from which side branches (i.e., carotids, innominate, subclavian, intercostals, superior mesenteric, celiac, renal) extend. In fact, most endovascular grafting systems have been in the treatment of infra-renal aneurysms, with or without the involvement of the iliac arteries. There are numerous examples in the prior art of endovascular grafting method and systems useable to treat such infra-renal aneurysms, with or without iliac artery involvement.

Patent Application Publication No. 2002/0103495 and U.S. Pat. No. 6,352,543 (Cole) disclose methods and devices for forming an anastomosis between hollow bodies using magnetic force to couple anastomotic securing components 78, 80 and create a fluid-tight connection between the lumens of the hollow bodies. End-to-side, side-to-side, and end-to-end anastomoses can be created without using suture or any other type of mechanical fasteners, although any such attachment means may be used in conjunction with the magnetic attachment The securing components have magnetic, ferromagnetic, or electromagnetic properties and may include one or more materials, for example, magnetic and nonmagnetic materials arranged in a laminated structure. As shown in FIG. 9A, the securing component 78 includes two members, 78A, 78B disposed on opposite surfaces of a wall of one of the hollow bodies. FIGS. 19A-19C show an embodiment in which one of the securing components has a flange-type construction. The system of anastomotic securing components may be used in many different applications including the treatment of cardiovascular disease, peripheral vascular disease, forming AV shunts for dialysis patients, etc., and may be sized and configured for forming an anastomosis to a specific hollow body, for example, a coronary artery or the aorta.

Patent Application Publication No. 2002/0143347 (Cole et al.) discloses methods and devices using magnetic force to form an anastomosis between hollow bodies. End-to-side, side-to-side, and end-to-end anastomoses can be created without using sutures or any other type of mechanical fasteners, although such attachment means may be used in practicing some aspects of the invention. Magnetic anastomotic components may be attached to the exterior of a vessel, e.g., by adhesive, without extending into the vessel lumen. Various magnetic component configurations are provided and may have different characteristics, for example, the ability to match the vessel curvature or to frictionally engage the vessel. FIG. 5B shows sutures S used to attach the component 16 to a vessel V, although it is stated that any suitable mechanical fastener may be used, e.g., clips, stents, barbs, hooks, wires, etc. FIG. 8B shows a magnetic anastomotic component 50 having an opening 52 and attachment structure 54 to facilitate securing the component to a vessel (not shown). As above, the structure 54 may be used alone or in combination with other means for securing the component to the vessel. In the illustrated embodiment, the attachment structure 54 is affixed to the component 50 to define a plurality of openings 56 which may be use to receive sutures, clips, clamps, pins, barbs, or other securing or fastening means.

Patent Application Publication No. 2001/0041902 (Lepulu et al.) discloses anastomotic methods and devices for placing a target vessel in fluid communication with a source of blood. FIGS. 11 and 12 show an embodiment utilizing magnets to secure the target vessel wall. In FIG. 11, a first securing component 90, preferably having a rectangular shape with rounded ends, is formed of magnetic material (or provided with magnetic material), as is a second securing component 92. The poles of the magnets are arranged to attract the components 90, 92 to one another and capture the tissue of the target vessel wall. FIG. 12 shows another embodiment wherein a first securing component 94 is carried by a conduit body 96, which is provided with a magnetic collar 98. A second securing component 100 has a magnetic collar 102, the poles of these magnets being arranged to repel the collars and force the components 94, 100 together.

U.S. Pat. Nos. 5,989,276 and 6,293,955 and Patent Application Publications Nos. 2003/0014061, 2003/0014062, 2003/0014063, 2001/0051809, and 2002/0052637 (Houser et al.) disclose a bypass graft incorporating fixation mechanisms at its opposite ends, for securing these ends to different locations along a blood vessel, or alternatively to different locations wherein one of the locations is a different vessel or an organ defining a cavity. Mechanical fixation features such as collets or grommets can be employed, enhanced by delivery of an electrical current sufficient to heat surrounding tissue to form a thermal bond. A graft deployment system includes a tissue dilator and a needle for perforating tissue, mounted coaxially within the dilator. Intraluminal systems further include a catheter for containing the dilator. To further assist positioning, magnets may be incorporated into the dilator near its distal tip, as indicated at 206 for a dilator 208 shown in FIG. 25. Such magnets may be formed of ferrite materials, or alternatively may be formed by winding conductive coils around the dilator to form electromagnets when current is supplied. The dilator magnets are used in conjunction with a guide wire 209 advanced beyond a stenosed lesion 210 within a vessel 212. The guide wire is formed of metal, and to further enhance magnetic attraction may incorporate a magnet 214 of opposite polarity to the dilator magnet. Magnetic positioning is stated to facilitate placing bypass grafts through tortuous vessels or over long distances beyond the lesion.

Houser et al. also disclose tissue dilators of deployment systems for graft fixation. Magnets may be incorporated into the dilator near its distal tip, as indicated at 206 for a dilator 208 shown in FIG. 25. Such magnets may be formed of ferrite materials, or alternatively may be formed by winding conductive coils around the dilator to form electromagnets when current is supplied. The dilator magnets are used in conjunction with a guide wire 209 advanced beyond a stenosed lesion 210 within a vessel 212. The guide wire is formed of metal, and to further enhance magnetic attraction may incorporate a magnet 214 of opposite polarity to the dilator magnet. Magnetic positioning is stated to facilitate placing bypass grafts through tortuous vessels or over long distances beyond the lesion.

U.S. Pat. Nos. 6,074,416 and 6,451,048 and Patent Application Publication No. 2002/0151913 (Berg et al.) disclose connector structures 34 for attaching elongated flexible tubular grafts to the body organ tubing of a patient. The connector structures are formed from nitinol wire.

U.S. Pat. No. 6,068,654 (Berg et al.) discloses a two-piece graft connector having a tubular band section with its proximal end configured to attach to a tubular graft and retention loops extending from its distal end, and a tubular anchor structure configured to be placed in the patient's tubular body tissue structure. The retention loops 26 can be made of nitinol wire. In one embodiment (see FIG. 1), the proximal end of the tubular band section is attached to a tubular graft. The retention loops extend from the distal end of the tubular band section of the connector, through an aperture in the side wall of a patient's tubular body tissue structure, and the tubular anchor structure is placed in the patient's tubular body tissue structure, within the retention loops. In another embodiment (see FIG. 9), retention loops 26 are replaced by relatively thicker retention fingers 70, which do not form loops, but instead form arcs, extending partially around the circumference of tubular body structure 11.

Methods for graft placement are disclosed in Patent Application Publications Nos. 2002/0143383 (Parodi) and 2002/0072790 (McGuckin, Jr. et al.) and U.S. Pat. No. 6,428,565 (Wisselink). Wisselink also describes the problems associated with using a conventional endovascular stent graft when the neck is too short (see the paragraph bridging columns 2 and 3).

With reference to FIGS. 15a-21, U.S. Pat. No. 6,068,637 (Popov et al.) discloses a method and devices for performing end-to-side anastomoses between the severed end of a first hollow organ and the side-wall of a second hollow organ utilizing a modified cutter catheter which is introduced into the first hollow organ in combination with a receiver catheter which is introduced into the second hollow organ. The distal end of the receiver catheter includes a receiver cavity and a selectively activatable magnetic material. The magnetic material is selected so that it will interact with a magnetically susceptible material disposed in the distal end of the modified cutter catheter when the modified cutter catheter is disposed in proximity to the proposed site for anastomosis whereby the severed end of the first hollow organ is matingly engaged with the sidewall of the second hollow organ. Thereafter, the severed end of the first hollow organ can be attached in sealing engagement with the side-wall utilizing clips, a biocompatible glue, or other suitable methods. The cutter is then activated to remove a portion of the side-wall of the second hollow organ, thereby creating an opening within the region of securement and establishing the anastomosis. In the preferred embodiment, the portion of the sidewall of the second hollow organ is engaged in the receiver cavity by the attractive force between the magnetically susceptible material and the magnetic material. The magnetically susceptible material is then released from the modified cutter catheter and withdrawn along with the portion of the sidewall removed by the cutter when the receiver catheter is withdrawn from the second hollow organ.

Most, if not all, of the endovascular grafts that have been designed for use in treating infra-renal aneurysms require that a proximal neck of adequate length exists inferior to the renal arteries, in order to provide a region where the superior end of the graft may be securely anchored so that blood flow to the renal arteries is not restricted. The deployment of an endovascular graft within the regions of the aorta from which the branch anatomic conduits emanate presents an additional technical challenge, because in those cases, the endovascular graft must be designed such that it can be inserted, aligned, and deployed with discrete maintenance of blood flow to the side branch anatomic conduits by means of additional branch grafts that arise from the newly-constructed endoaortic graft. This should be done in a manner that maintains sufficient blood flow to the branch anatomic conduit and yet exclude the aneurismal segment of the aorta from the haemodynamic consequences.

U.S. Pat. No. 5,425,765 (Tifenbrun et al.) discloses an endovascular graft that has one or more openings or fenestrations formed at specific locations, to allow blood to flow from the aorta into one or more of the branch arteries. However, such fenestrations do not form discrete connections with the branch arteries through which blood flows into the branch anatomic conduits. As a result, the area surrounding the fenestrations is prone to leakage of blood around the fenestrations, which might lead to migration of the graft as well as exposing that segment of aorta to the systemic blood pressure and other systemic hemodynamic effects. This defeats the entire concept of treatment of aneurismal disease, as the aortic wall is not entirely excluded after placement of the endoluminal graft. The migration of the endoluminal graft that might occur due to leakage around the fenestration might also compromise the blood flow to the branch anatomic conduit.

U.S. Pat. No. 6,428,565 (Wisselink et al.) discloses an endovascular graft that forms connections with the branch anatomic conduit with separate conduits. However, the technique and methods disclosed by Wisselink et al. have inherent deficiencies in more than one area. Wisselink et al. use conventional x-ray imaging techniques to introduce the grafts into the human body, but do not describe the delivery system and the technique of delivery such that it would make the procedure safer and most efficient. The use of conventional radiological methods to position a stent, graft, or prostheses is routine, but in this instance, the landing zone is very limited. Thus, in conjunction with fluoroscopy, an additional technique is required to align the endoaortic graft with the branch anatomic conduit and position the branch graft in such a manner that once completed, a conduit is created that supplies the branch anatomic conduit with unhampered blood flow. Wisselink et al.'s method for coupling of the branch graft to the aortic graft is prone to dislodgement thus prone to leakage of blood around the prosthesis. This will also promote graft migration. Post-implant migration and leakage may lead to obstruction of blood flow to the branch anatomic conduits.

U.S. Pat. No. 6,352,543 (Cole et al.) discloses a method of forming anastomosis between two hollow bodies, and the use of magnetic force as a coupling force to form a fluid tight junction. Cole et al.'s method in all its embodiments uses magnetic material as an anastomotic securing force and thus forms the actual fluid tight connections. However, this technique causes a rigid connection between two hollow organs that may lead to potential problems due to their fixed nature, and in the event of anastomotic narrowing are not amenable to interventional techniques in correcting the problems. Cole et al.'s method uses magnetic force as a method of attachment and refers to it as the means of anastomosis.

Thus, in view of the above-discussed limitations and shortcomings, there remains a need in the art for development of new endovascular grafting systems and methods which (a) may be useable for endovascular grafting in regions of the aorta where branch anatomic conduits (e.g., subclavian, innominate, carotid, intercostals, celiac, mesenteric, renals and iliac arteries) extend, and/or (b) may enable more aortic aneurysms patients to be candidates for endovascular repair, and/or (c) may advance the state of the art of endovascular grafting to improve patient outcomes or lessen complications.

It is to the solution of these and other problems that the present invention is directed.

SUMMARY OF THE INVENTION

It is accordingly a primary object of the present invention to extend the benefit of endoluminal grafting to a large population of patients that suffer with aneurismal disease of the aorta that involves its major branches.

It is another object of the present invention to provide a system and method for endoluminal grafting of a blood vessel or other anatomic conduit, in a region where one or more branch anatomic conduits (e.g., side branches, furcating, etc.) extend from the main anatomic conduit.

It is still another object of the present invention to provide endovascular grafting systems and methods which (a) may be useable for endovascular grafting in regions of the aorta where branch anatomic conduits (e.g., subclavian, innominate, carotid, intercostals, celiac, mesenteric, renals and iliac arteries) extend, and/or (b) may enable more aortic aneurysms patients to be candidates for endovascular repair, and/or (c) may advance the state of the art of endovascular grafting to improve patient outcomes or lessen complications.

These and other objects of the invention are provided by a system and method for endoluminal grafting of a main anatomic conduit in its diseased state in which it dilates to pose a life threatening condition (e.g., aortic aneurysms) and its various conduits (e.g., side branch anatomic conduits such as the left common carotid, subclavian, innominate, intercostals, superior mesenteric, celiac, or renal arteries or bifurcation such as the iliac arteries) that emanate from the main anatomic conduit.

The grafting system comprises 1) an endoaortic graft (endoaortic cuff) having at least one opening therein and 2) at least one branch graft that is passable through the opening of the endoaortic graft into the branch anatomic conduit(s) such that the junction between the branch graft and the endoaortic graft is substantially fluid tight.

In one aspect, the invention comprises a system and method for delivery of the endoaortic graft and also a system and method for efficient alignment and deployment of the branch (e.g., side branch) graft such that the coupling of the branch graft with the endoaortic graft is efficient and exact and fluid-tight.

In another aspect, the invention comprises a system and method for coupling the branch conduit to the endoaortic graft via a coupling mechanism employing a memory metal alloy. Two different embodiments of coupling mechanisms are provided, the coupling mechanism being chosen depending on the site and anatomic location of the branch conduit. In one embodiment, the coupling mechanism is incorporated in the endoaortic graft and in the other embodiment, the coupling mechanism is incorporated in the endobranch graft.

In still another aspect, the invention comprises a system and method for the proper and exact alignment of the endoaortic graft and the branch conduit using magnetic force of a suitable nature, and which does not use the magnetic force as the coupling mechanism.

Other objects, features and advantages of the present invention will be apparent to those skilled in the art upon a reading of this specification including the accompanying drawings.

BRIEF DESCRIPTION OF THE DRAWINGS

The invention is better understood by reading the following Detailed Description of the Preferred Embodiments with reference to the accompanying drawing figures, in which like reference numerals refer to like elements throughout, and in which:

FIGS. 10A-10DD illustrate the steps in the method for endoluminal grafting of blood vessels or other tubular, main anatomic conduits, in a region where one or more branch anatomic conduits extend from the main anatomic conduit, using the endoatoric graft, the endoaortic graft delivery system, the branch anatomic graft, and the branch graft delivery system in accordance with the present invention.

DETAILED DESCRIPTION OF THE PREFERRED EMBODIMENTS

In describing preferred embodiments of the present invention illustrated in the drawings, specific terminology is employed for the sake of clarity. However, the invention is not intended to be limited to the specific terminology so selected, and it is to be understood that each specific element includes all technical equivalents that operate in a similar manner to accomplish a similar purpose.

The present invention provides a system and method for endoluminal grafting of a blood vessel or other native, main anatomic conduit, in a region where one or more branch anatomic conduits (e.g., side branches, furcating, etc.) extend from the main anatomic conduit.

Figures 3A, 3B, 4A:
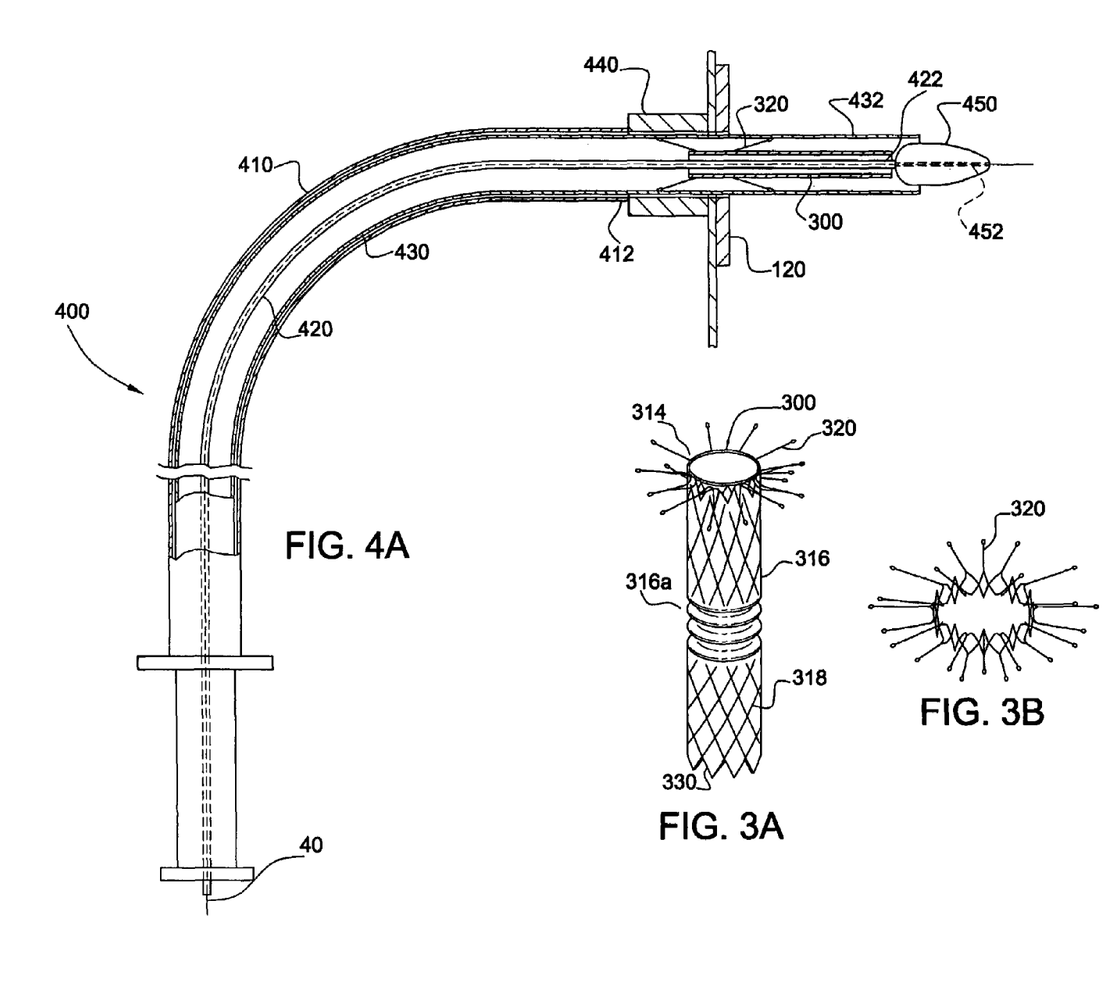
FIG. 3A is a side elevational view of a branch graft in accordance with a first embodiment of the present invention.
FIG. 3B is an enlarged perspective view of the connector mechanism of the branch graft of FIG. 3A, for coupling the branch graft with the endoaortic graft of FIG. 1A, in the deployed position.
FIG. 4A is a cross-sectional view of a delivery system for introducing the branch graft into a branch anatomic conduit of a main anatomic conduit in accordance with a first embodiment of the present invention.
Figure 4B:
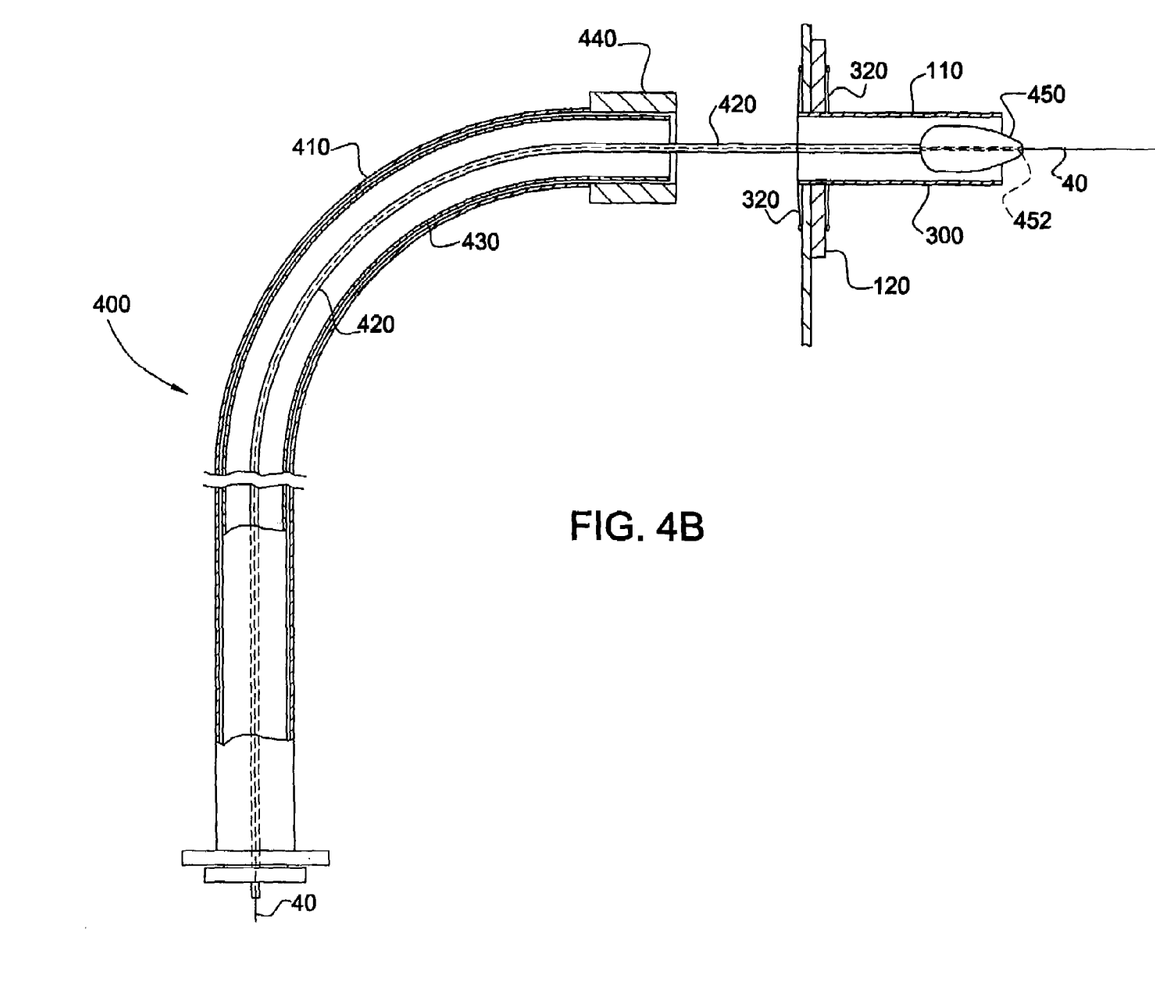
FIG. 4B is a cross-sectional view of the delivery system of FIG. 4A, in which the branch graft has been deployed.

In accordance with a first embodiment of the present invention, the endoluminal grafting system 50 comprises an endoaortic graft 100 (also referred to herein as an "endoaortic cuff") (FIGS. 1A-1B), an endoaortic graft delivery system 200 for introducing the endoaortic graft 100 into a native, main anatomic conduit 10 (FIGS. 2A-2C), a branch graft 300 (FIG. 3), and a branch graft delivery system 400 for housing the branch graft 300 and introducing it into a branch anatomic conduit 20 extending from the main anatomic conduit 10 (FIGS. 4A-4B).

Figures 1A, 1B, 2A, 2B, 2C:
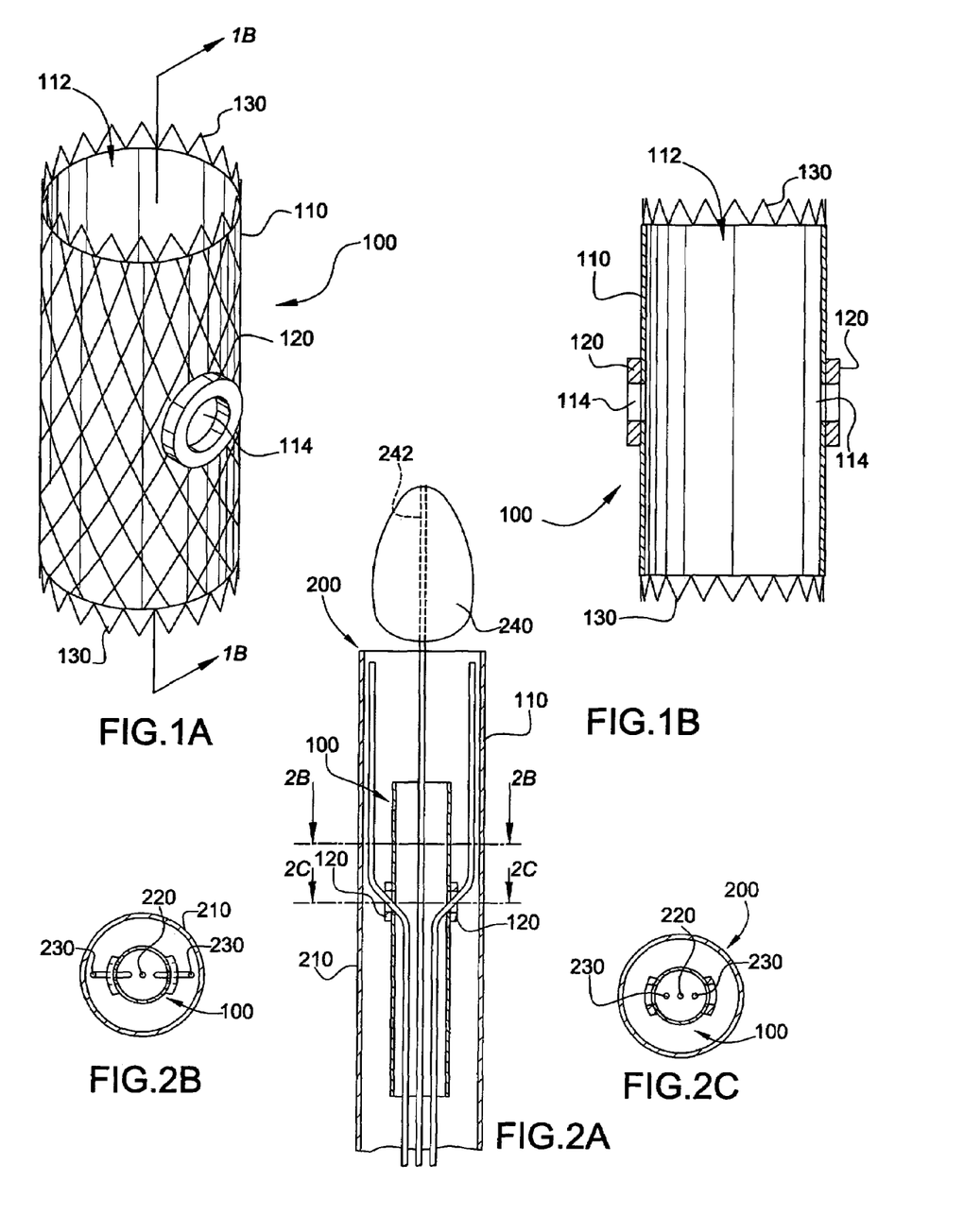
FIG. 1A is a perspective view of a first embodiment of an endoaortic graft in accordance with the present invention.
FIG. 1B is a cross-sectional view of the endoaortic graft of FIG. 1.
FIG. 2A is a cross-sectional view of a delivery system for introducing the endoaortic graft of FIGS. 1A-1B into a native, main anatomic conduit in accordance with first and second embodiments of the present invention.
FIG. 2B is a cross-sectional view taken along line 2B of FIG. 2A.
FIG. 2C is a cross-sectional view taken along line 2C of FIG. 2A.

As shown in FIGS. 1A-1B, the endoaortic graft 100 comprises a first pliable tube (i.e., a tube formed of a pliable material) having a lumen 112 extending longitudinally therethrough; at least one branch opening 114 (e.g., an aperture) formed in the first pliable tube 110; a flexible magnetic ring 120 incorporated around the at least one branch opening 114 of the first pliable tube 110; and an endoaortic graft anchoring device 130 for holding the first pliable tube 110 in substantially fixed place within the main anatomic conduit 10, such that the branch opening 114 is in alignment with the branch anatomic conduit 20. The pliable material can be woven polyester, expanded polytetrafluroethalene (ePTFE), and other pliable, biocompatible materials. The endoaortic graft anchoring device 130 can be, but is not limited to, such conventional devices as a radially expandable stent, a frame, a series of rings, and/or adhesive sutures, staples, etc.

Figures 7A, 7B, 8B:
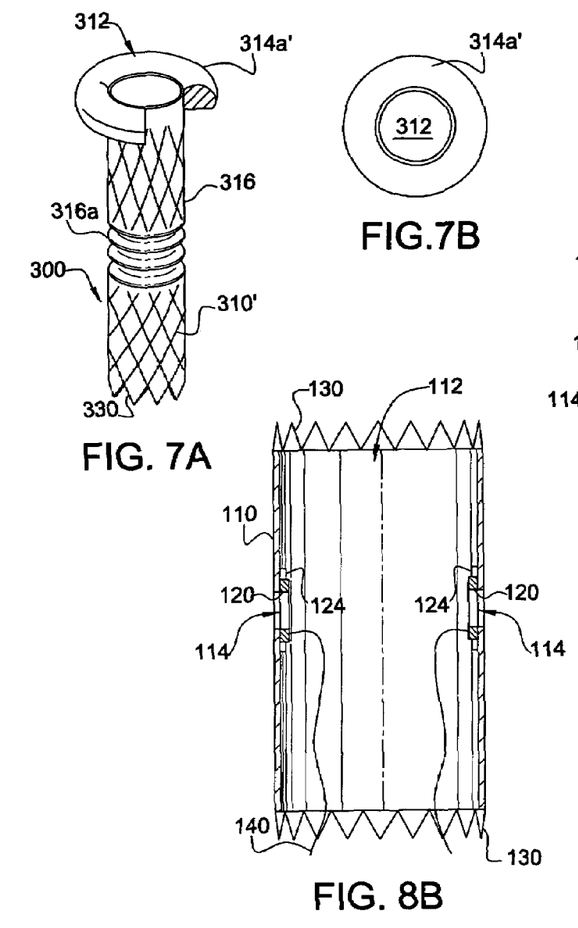
FIG. 7A is a side elevational view of a branch graft in accordance with a second embodiment of the present invention.
FIG. 7B is a top elevational view of the branch graft of FIG. 7A.
FIGS. 8A and 8B are cross-sectional views of second embodiment of an endoaortic graft in accordance with the present invention, with different attachment mechanisms for the magnetic ring.
Figure 8A:
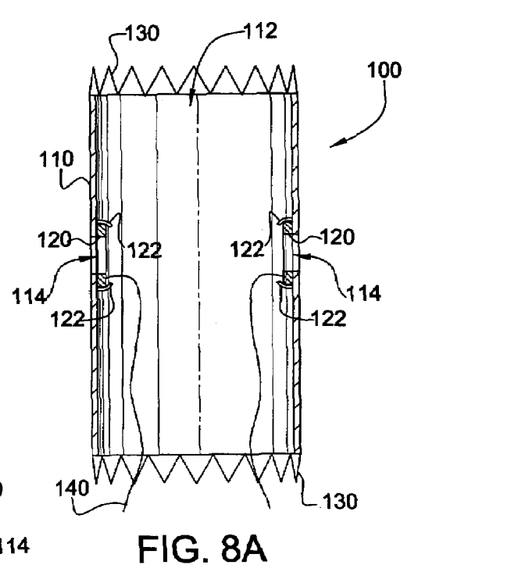

The endoaortic graft 100 of the first embodiment of the invention can have several embodiments. In a first embodiment, shown in FIGS. 1A-1B, the flexible magnetic ring 120 is positioned on, and is permanently secured to, the exterior surface of the first pliable tube 110. In a second embodiment, shown in FIGS. 8A and 8B, the flexible magnetic ring 120 is positioned on, and is removably secured to, the interior surface of the first pliable tube 110. The second embodiment may be preferable for smaller grafts or other situations where it may not be desirable to leave the magnetic ring in place. In the second embodiment, the flexible magnetic ring 120 can be removably secured to the interior surface of the first pliable tube 110 by flexible hooks 122 (FIG. 8A) or by a friction fit with a flexible bushing 124 secured to the interior surface of the first pliable tube 110 (FIG. 8B). One or more wires 140 are attached to the removable magnetic ring 120 for separating the removable magnetic ring 120 from the flexible hooks 122 or bushing 124 and withdrawing it from patient.

As shown in FIGS. 2A-2C, in accordance with the first embodiment of the invention, the endoaortic graft delivery system 200 comprises a flexible outer sheath 210, which functions as a delivery catheter, a flexible inner central sheath 220, at least one flexible inner side sheath 230, and a tapered and flexible tip 240 at the distal end of the inner central sheath 220, the tip 240 forming the nose cone of the delivery system. The inner central sheath 220 is substantially concentric with the outer sheath 210 for carrying an axial guide wire 30 (shown in FIGS. 10A-10J). The at least one inner side sheath 220 is radially positioned between the inner central sheath 220 and a corresponding branch opening 114 in the first pliable tube 110 for carrying a corresponding separate branch anatomic conduit guide wire 40 (shown in FIGS. 10C-10J) that is to be passed into a corresponding side branch anatomic conduit 20. The tapered, flexible tip 240 has an aperture 242 to allow the passage of the axial guide wires 30 therethrough. The endoaortic graft 100 is loaded in the endoaortic graft delivery system 200 such that the central sheath 220 carrying the axial guide wire 30 is centrally located therethrough, and the at least one inner side sheath 220 carrying a corresponding branch guide wire 40 to a corresponding branch anatomic conduit 20 is positioned within the first pliable tube 110 downstream of the branch opening 114 and traverses through the branch opening 114.

As shown in FIG. 3A the branch graft 300 in accordance with the first embodiment of the invention comprises a second pliable tube 310 (i.e., a tube formed of a pliable material) having a lumen 312 extending therethrough and having a proximal end 314, a mid-portion 316, and a distal end 318; a connector mechanism 320 at the proximal end; and a branch graft anchoring device 330 at the distal end 318. The second pliable tube 310 is sized to be receivable through the flexible magnetic ring 120 of the endoaortic graft 100 such that the junction between the branch graft 300 and the endoaortic graft 100 is substantially fluid tight. The pliable material can be woven polyester, expanded polytetrafluroethalene (ePTFE), or other pliable, biocompatible material. The connector mechanism 320 is made from a memory metal (such as nitinol) and is associated with the proximal end of the second pliable tube. When activated, the connector mechanism 320 is able to form a connection with the corresponding branch opening 114 in the first pliable tube 110, such that the fluid that flows through the lumen 112 of the first pliable tube 110 can pass through the branch opening 114 in the first pliable tube 110 and into the lumen 312 of the branch graft 300. The mid-portion 316 is configured with a corrugated section 316a to maintain a patent lumen of the second pliable tube 310, such that the branch graft 300 is kink-resistant in an angular situation. The branch graft anchoring device 330 is operative to hold at least the distal end 318 of the branch graft 300 in contact with the surrounding wall of the branch anatomic conduit 20. The branch graft anchoring device 330 can be, but is not limited to, a radially expandable stent, a frame, hooks, rings, sutures, staples, and/or adhesive, staples.

As shown in FIGS. 4A-4B, in accordance with the first embodiment of the invention, the branch graft delivery system 400 comprises an arrangement of three substantially concentric, flexible, hollow sheaths, an outer sheath 410, an inner sheath 420, and a middle sheath 430 between the outer and inner sheaths 410 and 420. Prior to deployment, the distal ends 422 and 432 of the inner and middle sheaths 420 and 430 are substantially coterminous, and the branch graft 300 is housed between the inner sheath 420 and the middle sheath 430, so that the middle sheath 430 also covers the branch graft 300. The outer sheath 410 cannot be retracted. At its distal end 412, the outer sheath 410 carries a magnet 440. The magnet 440 can have either a natural or an induced magnetic field, and can include an electromagnet, a ferromagnet, or a ferromagnetic fluid contained within a collar. The outer sheath 410 can also rotate so as to change the polarity of the magnet 440 in a particular plane, in order to disengage the branch graft delivery system 400 from the endoaortic graft 100. The inner sheath 420 accommodates the guide wire going 40 into the branch anatomic conduit 20 so that the entire branch graft delivery system 400 can be passed over the guide wire 40. The distal end 422 of the inner sheath 420 terminates in a tapered and flexible tip 450 forming the nose cone of the branch graft delivery system 400. The tapered, flexible tip 450 has an aperture 452 therein to allow the passage of a guide wire 40 therethrough.

Because the middle sheath 430 covers both the inner sheath 420 and the branch graft 300, when the middle sheath 430 is retracted, it will uncover the branch graft 300 such that the branch graft 300 is deployed fully to form the new connection with the endoaortic graft 100.

The branch graft delivery system 400 in accordance with the first embodiment of the invention is suited primarily for use in axial (straight line) situations, because the distal end is not particularly flexible.

Figure 10:
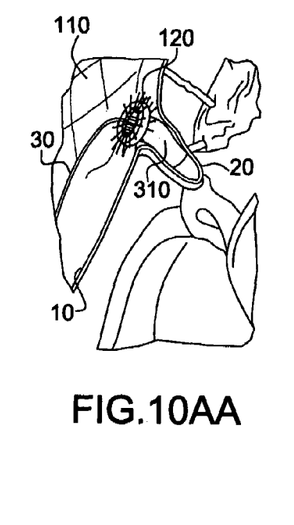
Figure 10A:
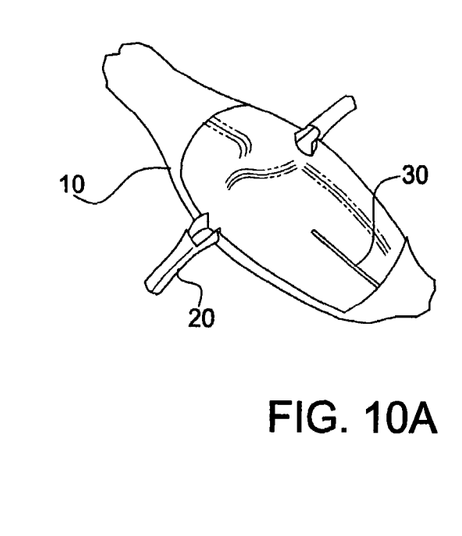
Figure 10B:
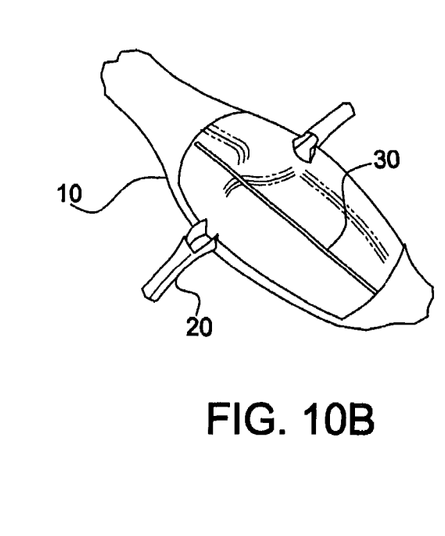
Figure 10C:
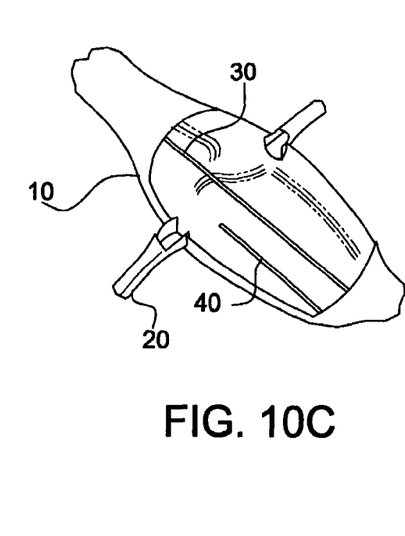
Figure 10D:
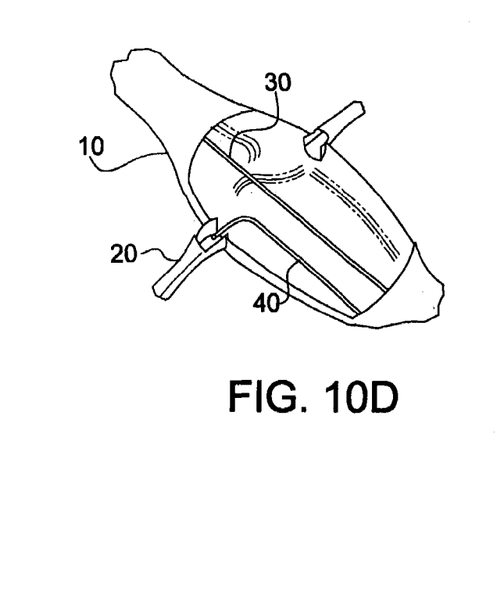
Figure 10E:
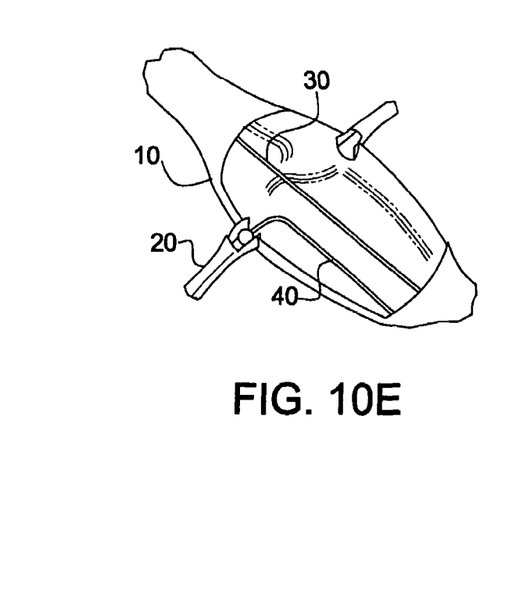
Figure 10F:
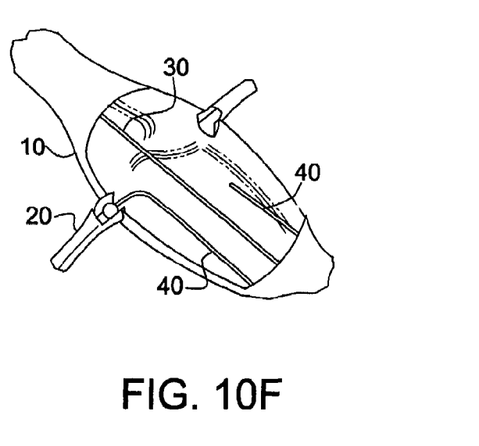
Figure 10G:
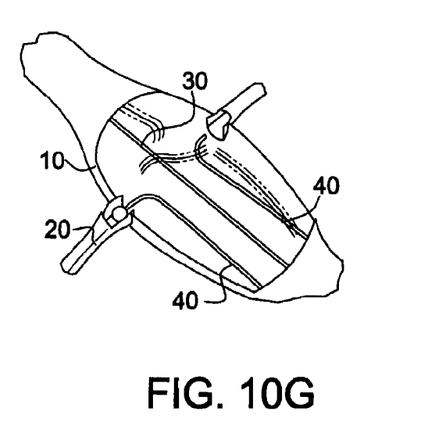
Figure 10H:
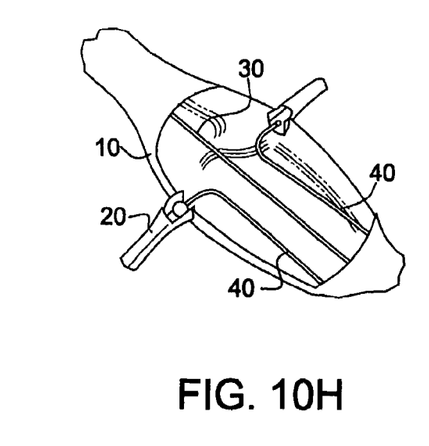
Figure 10I:
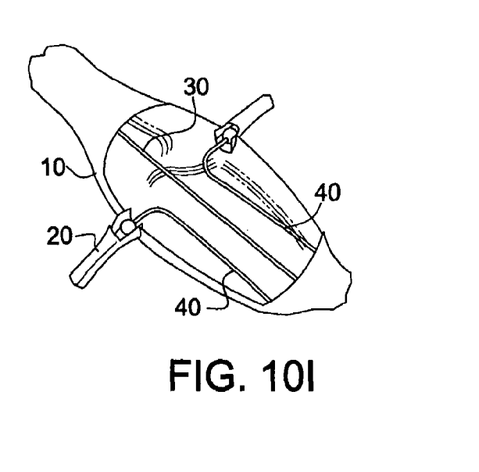
Figure 10J:
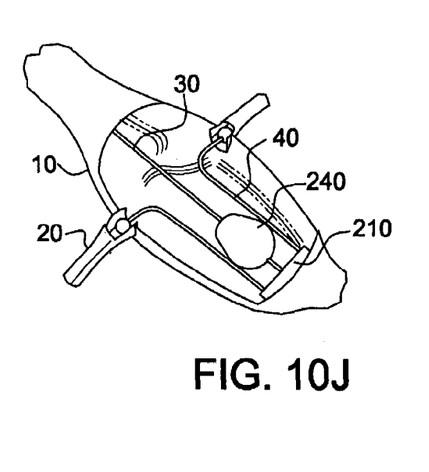
Figure 10K:
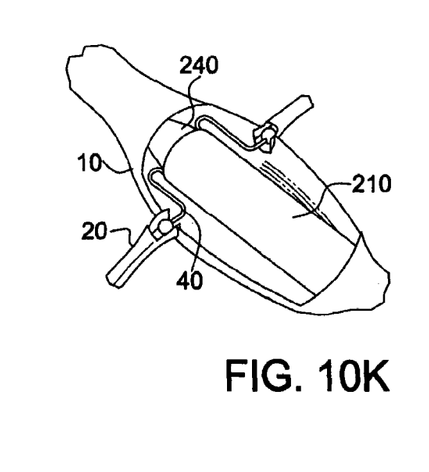
Figure 10L:
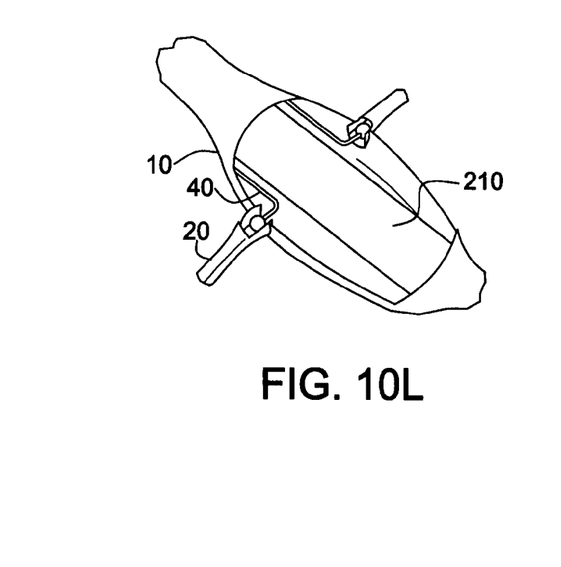
Figure 10M:
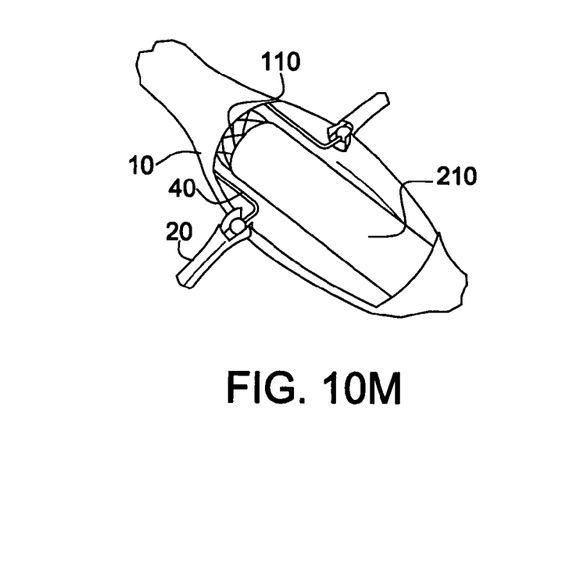
Figure 10N:
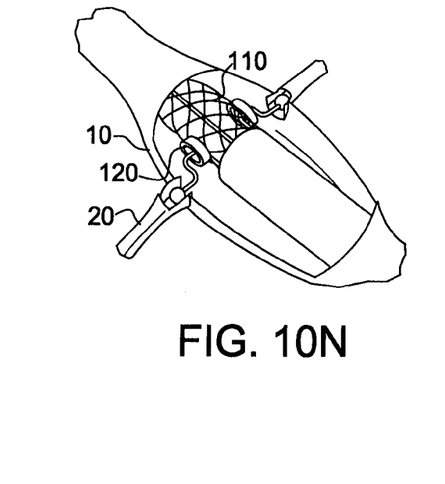
Figure 10O:
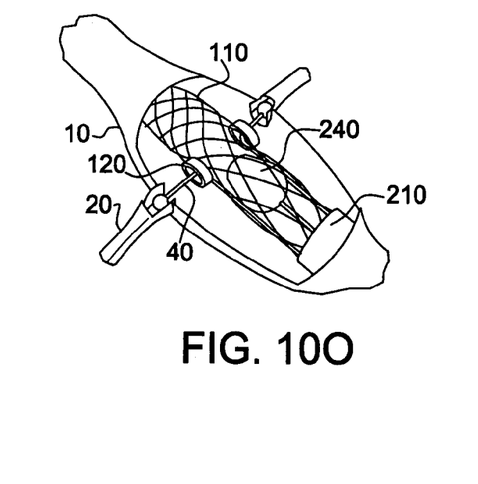
Figure 10P:
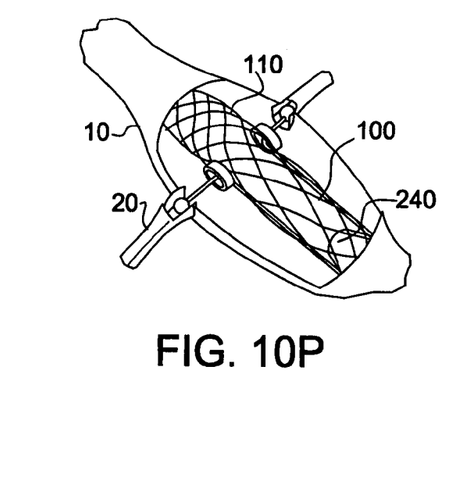
Figure 10Q:
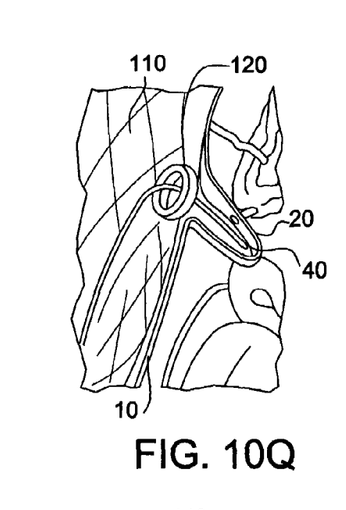
Figure 10R:
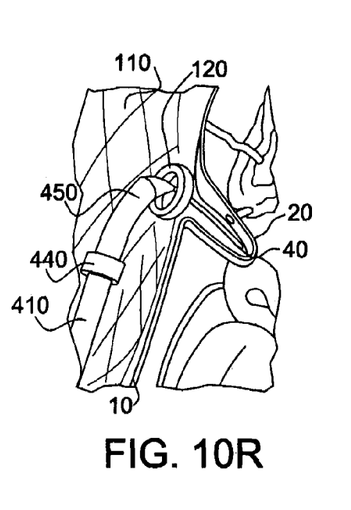
Figure 10S:
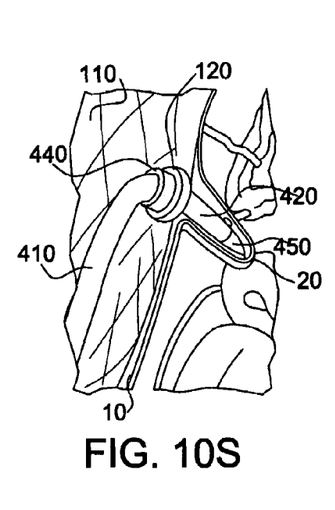
Figure 10T:
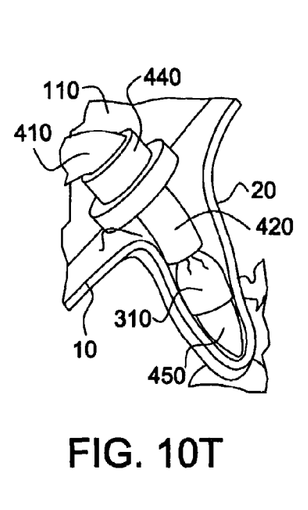
Figure 10U:
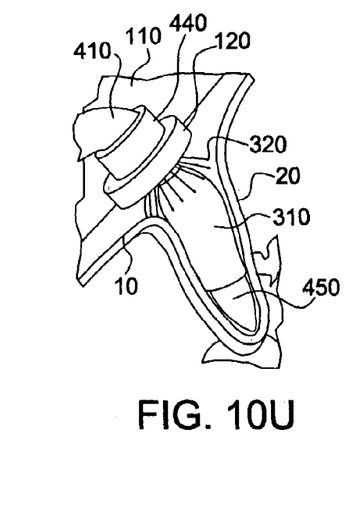
Figure 10V:
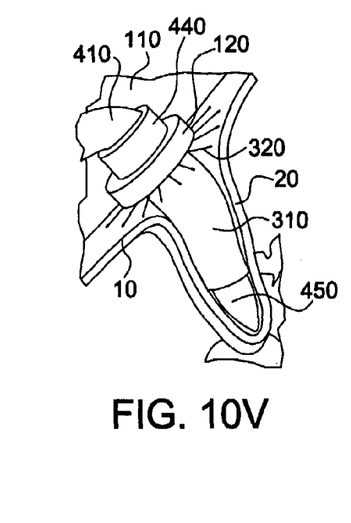
Figure 10W:
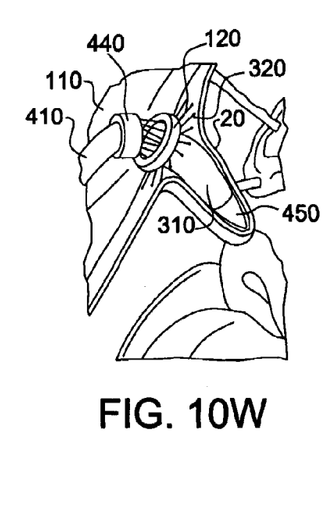
Figure 10X:
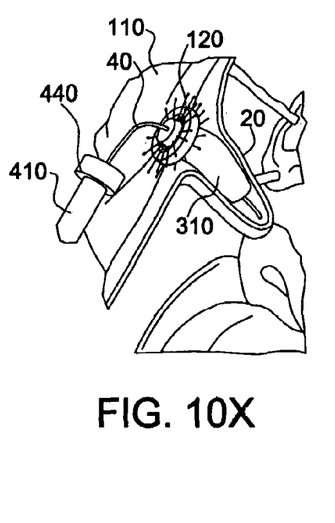
Figure 10Y:
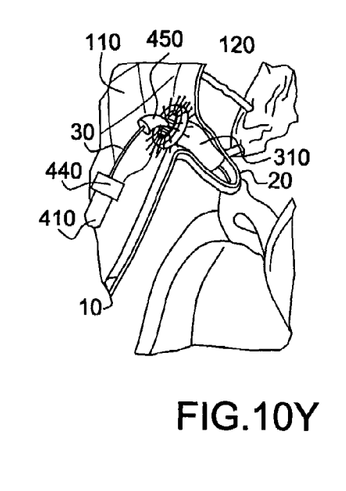
Figure 10Z:
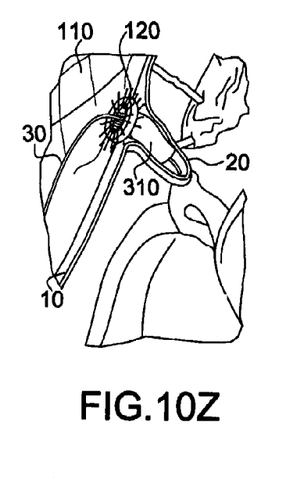

The above-described endoluminal grafting system 50 in accordance with the first embodiment of the present invention can be implanted within the branched anatomic conduit by a method comprising the following steps:

1) Advancing an axial guide wire 30 into the body of the aneurysm (FIGS. 10A-10B), and then advancing at least one other, more pliable balloon tipped guide wire 40 into the branch anatomic conduit using the endoaortic graft delivery system 200 (FIGS. 10C-10I);
2) Transluminally advancing the endoaortic graft 100 over the guide wires 30 and 40 into the branched, main anatomic conduit 10 using the endoaortic graft delivery system 200 (FIGS. 10J-10M;
3) Positioning the endoaortic graft 100 within the anatomic conduit 10 using the endoaortic graft delivery system 200 such that the branch opening 114 is aligned with the branch anatomic conduit 20 (FIGS. 10N-10P);
4) Utilizing the endoaortic graft anchoring device 130 to anchor the endoaortic graft 100 within the main anatomic conduit 10 (not shown);
5) Transluminally advancing the branch graft 300 loaded in the branch graft delivery system 400 over the guide wire 40 to the branch anatomic conduit 20 (FIGS. 10Q-10R);
6) Passing the distal end of the branch graft delivery system containing the branch graft 300 through the branch opening 114 and into the branch anatomic conduit 20, until the magnetic ring 120 of the endoaortic graft 100 and the magnet 440 on the branch graft delivery system 400 attach (FIG. 10S);
7) Operating the branch graft delivery system 400 such that the branch graft 300 is deployed in the branch anatomic conduit 20, until such time as the retractable middle sheath 430 of the branch graft delivery system 400 is fully retracted (FIGS. 10T-10V);

8) Once the retractable middle sheath 430 of the branch graft delivery system 400 is fully retracted, rotating the outer sheath 410 of the branch graft delivery system 400 by 180 degrees to switch the magnetic poles to allow the two magnets 120 and 440 to disengage as well as deploy the most proximal part of the nitinol connector mechanism 320, allowing the leak proof connection between the branch graft 300 and the endoaortic graft 100 (FIGS. 10W-10DD).

In accordance with a second embodiment of the present invention, the endoluminal grafting system 50' comprises an endoaortic graft 100' (FIGS. 5A-5D), an endoaortic graft delivery system 200 for introducing the endoaortic graft 100' into a native, main anatomic conduit 10 (FIGS. 2A-2C), a branch graft 300' (FIGS. 7A-7B), and a branch graft delivery system 400 for housing the branch graft 300' and introducing it into a branch anatomic conduit 20 extending from the main anatomic conduit 10 (FIGS. 4A-4B).

Figure 5A:
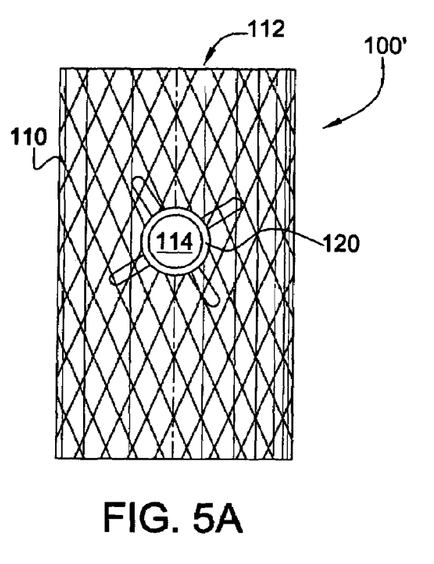
FIG. 5A is a partial perspective view of the outside of an endoaortic graft in accordance with a second embodiment of the present invention.
Figure 5B:
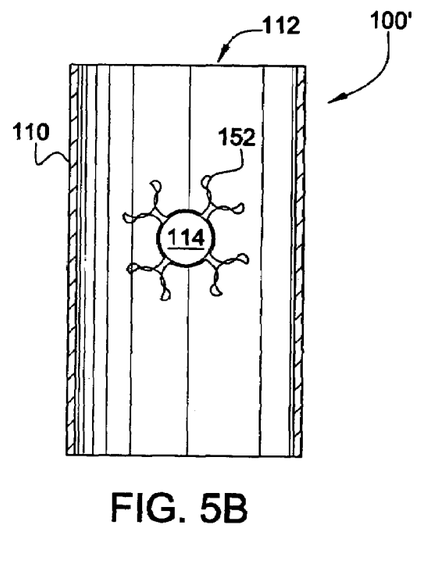
FIG. 5B is a partial perspective view of the inside of the endoaortic graft of FIG. 5A with the coupling mechanism for coupling with the branch graft in the open position, the struts and the magnetic ring being omitted for clarity.
Figure 5C:
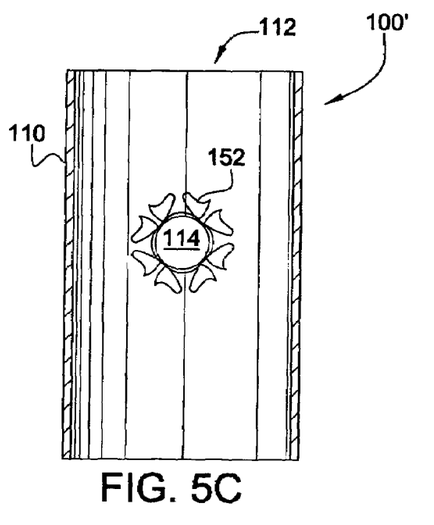
FIG. 5C is a partial perspective view of the inside of the endoaortic graft of FIG. 5A with the coupling mechanism for coupling with the branch graft in the closed position, the struts and the magnetic ring being omitted for clarity.
Figure 5D:
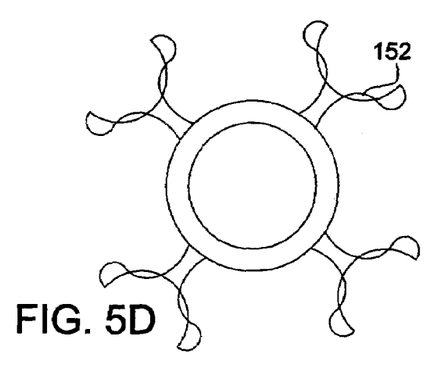
FIG. 5D is an enlarged view of the coupling mechanism for coupling with the branch graft of FIGS. 5B and 5C, in the closed position, the struts being omitted for clarity.
Figure 6A:
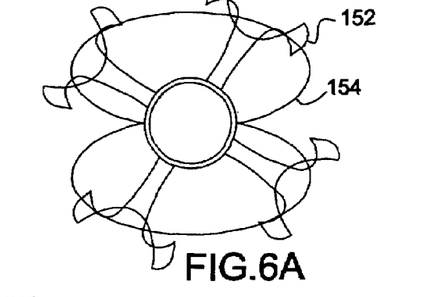
FIG. 6A is a view of the coupling mechanism of FIGS. 5B and 5C, in the open position, and its accompanying struts, the flexible magnetic ring being omitted for clarity.
Figure 6B:
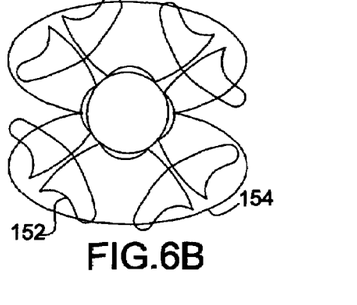
FIG. 6B is a view of the coupling mechanism of FIGS. 5B and 5C, in the closed position, and its accompanying struts, the flexible magnetic ring being omitted for clarity.

As shown in FIGS. 5A-5D, the endoaortic graft 100' comprises a first pliable tube 110 (i.e., a tube formed of a pliable material) having a lumen 112 extending longitudinally therethrough; at least one branch opening 114 (e.g., an aperture) formed in the first pliable tube 110; a flexible magnetic ring 120 incorporated around the at least one branch opening 114 of the first pliable tube; a coupling mechanism 150 for coupling the branch graft 300' to the flexible magnetic ring 120; and an endoaortic graft anchoring device 130 for holding the first pliable tube 110 in substantially fixed place within the main anatomic conduit 10, such that the branch opening 114 is in alignment with the branch anatomic conduit 20. The pliable material can be woven polyester, expanded polytetrafluoroethalene (ePTFE), and other pliable, biocompatible materials. The coupling mechanism 150 is as shown in FIG. 5D and FIGS. 6A-6B, and comprises a plurality of staples 152 extending outwardly from the perimeter of the flexible magnetic ring 120, and a plurality of struts 154 that hold the staples 152 in the open position and are releasable to allow the staples 152 to close. The staples 152 preferably are made from a memory metal (such as nitinol). The endoaortic graft anchoring device 130 can be, but is not limited to, such conventional devices as a radially expandable stent, a frame, a series of rings, and/or adhesive sutures, staples, etc.

The endoaortic graft delivery system 200 of the second embodiment of the present invention is the same as shown and described in connection with the first embodiment.

As shown in FIGS. 7A-7B, the branch graft 300' comprises a second pliable tube 310' (i.e., a tube formed of a pliable material) having a lumen 312 extending therethrough, and having a collapsible, toroidal-shaped proximal end 314' defining a connector mechanism, a mid-portion 316, and a distal end 318; and a branch graft anchoring device 330 at the distal end. The pliable material can be woven polyester, expanded polytetrafluroethalene (ePTFE), or other pliable, biocompatible material. The toroidal proximal end 314' can be a hollow silastic ring filled with a ferro-fluid (that is, a fluid with magnetic particles suspended therein). The second pliable tube 310' is sized to be receivable through the flexible magnetic ring 120 of the endoaortic graft 100' such that the junction between the branch graft 400 and the endoaortic graft 100' is substantially fluid tight, and the ferro-fluid has sufficient magnetic properties to be attracted to the flexible magnetic ring 120 yet still be easily movable relative thereto. The mid-portion 316 is configured with a corrugated section 316a to maintain a patent lumen of the second pliable tube 310', such that the branch graft 300' is kink-resistant in an angular situation. The branch graft anchoring device 330 is positioned at the distal end 318 and is operative to hold at least the distal end 318 of the branch graft 300' in contact with the surrounding wall of the branch anatomic conduit 20. The branch graft anchoring device 330 can be, but is not limited to, a radially expandable stent, a frame, hooks, rings, sutures, staples, and/or adhesive, staples.

The branch graft delivery system 400 of the second embodiment of the present invention is the same as shown and described in connection with the first embodiment.

The above-described endoluminal grafting system 50' in accordance with the second embodiment of the present invention can be implanted within the branched anatomic conduit 10 by a method comprising the same steps (1) through (7) as in accordance with the first embodiment, and the following additional steps:

8) Once the retractable middle sheath 430 of the branch graft delivery system 400 is fully retracted, rotating the outer sheath 410 of the branch graft delivery system by 180 degrees to switch the magnetic poles to allow the two magnets 120 and 440 to disengage.

9) Withdrawing the branch graft delivery system 400;

10) Advancing another guidewire with a hook or snare mechanism through the lumen 112 of the endoaortic graft 100';

11) Under fluoroscopy, using the hook or snare mechanism to engage the struts 154 of the endoaortic graft coupling mechanism 150 and apply traction to them to deploy the staples 150 and engage the toroidal proximal end 314' of the branch graft 300'.

Figure 9A:
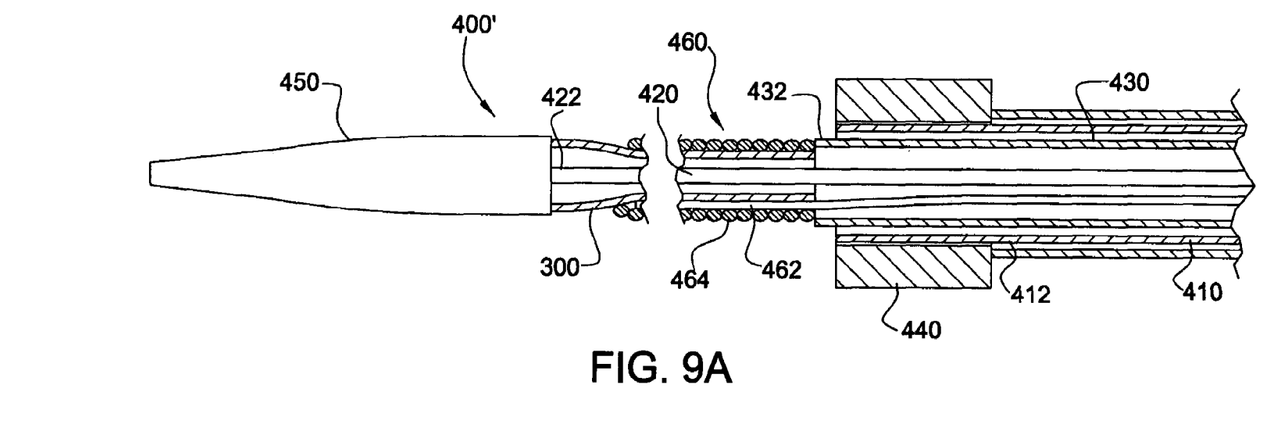
FIG. 9A is a cross-sectional view of a delivery system for introducing the branch graft of FIG. 7A into a branch anatomic conduit of a main anatomic conduit in accordance with another embodiment of the present invention.
Figure 9B:
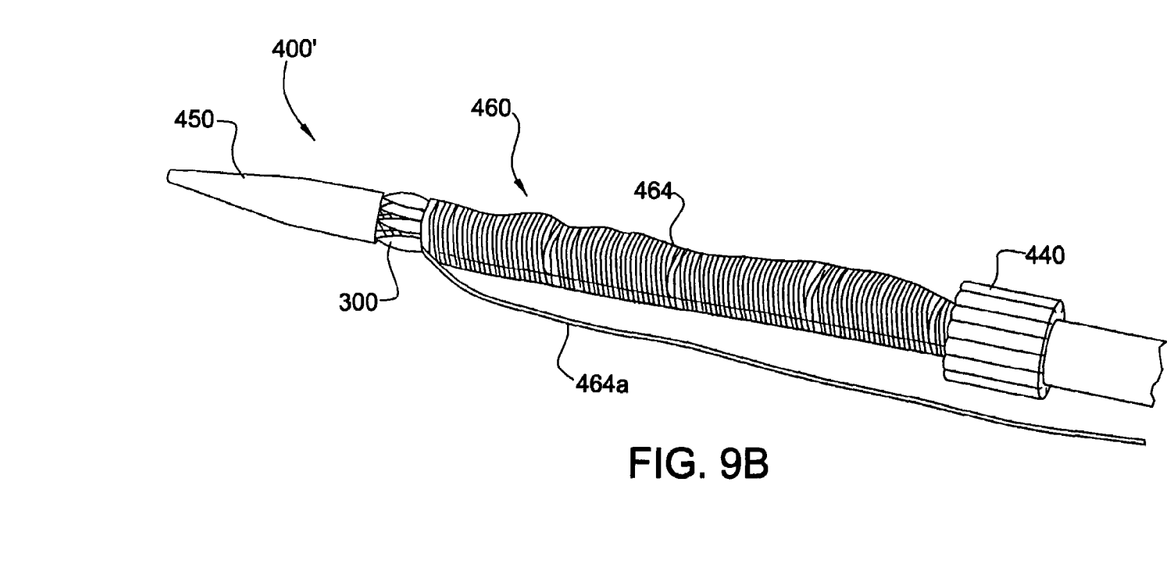
FIG. 9B is an enlarged perspective view of the distal end of the delivery system of FIG. 9A.

In accordance with a third embodiment of the present invention, the endoluminal grafting system 50" comprises the endoaortic graft 100 of FIGS. 1A-1B, 5A-5D or 8, the endoaortic graft delivery system 200 shown in FIGS. 2A-2C, a branch graft 300 as shown in FIG. 3, and a branch graft delivery system 400' shown in FIGS. 9A and 9B for housing and introducing the branch graft 300. The branch graft delivery system 400' of FIGS. 9A and 9B is similar to that of FIGS. 4A-4B in also comprising an arrangement of three substantially concentric, flexible, hollow sheaths, an outer sheath 410, an inner sheath 420, and a middle sheath 430 between the outer and inner sheaths, a magnet 440 carried at the distal end 412 of the outer sheath 410, and a nose cone 450 terminating the distal end 422 of the inner sheath 420. However, in the endoaortic graft delivery system 200 in accordance with the third embodiment of the invention, prior to deployment, the distal end 422 of the inner sheath 420 extends outwardly of the distal ends 412 and 432 of the outer and middle sheaths 410 and 430, with the branch graft 300 loaded over the distal end 432 of the middle sheath 430 with only the connector mechanism 320 housed between the outer and middle sheaths 410 and 430. Further, the branch graft delivery system 400' includes means 460 for maintaining the branch graft 300 in a contracted condition prior to deployment.

In the third embodiment of the invention, the means 460 for maintaining the branch graft 300 in a contracted position includes a deployment wire 462 radially positioned between the inner and middle sheaths 420 and 430, and a thread 464 wrapped around both the contracted branch graft 300 and the deployment wire 462. The thread 464 is made of a biodegradable, absorbable material (for example, PTF or synthetic, absorbable suture sold under the trademarks Vicryl® and Monocryl®). One end 464a of the thread 464 is left as a tail extending at least the length of the outer sheath 412 and the other end (not shown) is secured on itself, for example by a half-knot, to prevent the wrapping from unraveling. The thread 464 is wrapped about the deployment wire 462 and the branch graft 300 in a figure-eight configuration, so that when the deployment wire 462 is retracted, the wrapping unravels, allowing the branch graft 300 to assume an expanded condition.

The third embodiment of the invention, in which the branch graft delivery system 400' employs a wrapping, is particularly suited to use in a non-axial (curved) situation, as the distal end of the branch graft delivery system 400' is relatively flexible, although it can also be used in axial situations.

The above-described endoluminal grafting system 50" in accordance with the third embodiment of the present invention can be implanted within the branched anatomic conduit 10 by a method comprising the same steps (1) through (6) as in accordance with the first embodiment, and the following additional steps:

7) Operating the branch graft delivery system 400' such that the branch graft 300 is deployed in the branch anatomic conduit 20, until such time as the retractable middle sheath 430 of the branch graft delivery system 400' is fully retracted;

8) Once the retractable middle sheath 430 of the branch graft delivery system 400' is fully retracted, rotating the outer sheath 410 of the branch graft delivery system 400' by 180 degrees to switch the magnetic poles to allow the two magnets 120 and 440 to disengage as well as deploy the most proximal part of the nitinol connector mechanism 320, allowing the leak proof connection between the branch graft 300 and the endoaortic graft 100.

Modifications and variations of the above-described embodiments of the present invention are possible, as appreciated by those skilled in the art in light of the above teachings. It is therefore to be understood that, within the scope of the appended claims and their equivalents, the invention may be practiced otherwise than as specifically described.

What is claimed is:

1. A system for endoluminal grafting of a native, main anatomic conduit, in a region where at least one branch anatomic conduit extends from the main anatomic conduit, comprising:

an endoaortic graft including a first pliable tube having a lumen extending longitudinally therefrom, at least one branch opening formed in the first pliable tube, a flexible magnetic ring positioned around the at least one branch opening of the first pliable tube, and endoaortic graft anchoring means for holding the first pliable tube in substantially fixed place within the main anatomic conduit with the branch opening is in alignment with the branch anatomic conduit, the first pliable tube being made of a biocompatible material; and a branch graft including a second pliable tube having a proximal end, a mid-portion, a distal end, a lumen extending therethrough, connector means for connecting the proximal end with the branch opening of the first pliable tube to allow the fluid that flows through the lumen of the endoaortic graft to pass through the branch opening into the lumen of the branch graft, and branch graft anchoring means at the distal end for holding at least the distal end of the branch graft in contact with the surrounding wall of the branch anatomic conduit, the second pliable tube being made of a biocompatible material, wherein the connector means comprises a hollow elastic toroid filled with a ferro-fluid having sufficient magnetic properties to be attracted to the flexible magnetic ring yet still be easily movable relative thereto.

\* \* \* \* \*